US009000399B2

(12) United States Patent  
Kim et al.

(10) Patent No.: US 9,000,399 B2  
(45) Date of Patent: Apr. 7, 2015

(54) FLUORESCENCE DETECTING OPTICAL SYSTEM AND MULTI-CHANNEL FLUORESCENCE DETECTION APPARATUS INCLUDING THE SAME

(75) Inventors: Kyung-ho Kim, Seoul (KR); Joon-ho Kim, Seongnam-si (KR); Kak Namkoong, Seoul (KR); Won-seok Chung, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 804 days.

(21) Appl. No.: 13/271,101

(22) Filed: Oct. 11, 2011

(65) Prior Publication Data

US 2012/0280143 A1 Nov. 8, 2012

(30) Foreign Application Priority Data

May 3, 2011 (KR) ........................ 10-2011-0041994

(51) Int. Cl.  
*G01N 21/64* (2006.01)  
*G01J 3/44* (2006.01)  
*G01J 3/02* (2006.01)  
G01N 21/05 (2006.01)  
G01N 21/03 (2006.01)

(52) U.S. Cl.  
CPC ............. *G01N 21/645* (2013.01); *G01J 3/4406* (2013.01); *G01J 3/0237* (2013.01); *G01J 3/0208* (2013.01); *G01J 3/0229* (2013.01); G01N 21/05 (2013.01); G01N 2021/6419 (2013.01); G01N 2021/6421 (2013.01); G01N 2021/6478 (2013.01); G01N 2201/0635 (2013.01); G01N 2021/0346 (2013.01)

(58) Field of Classification Search  
CPC ..................................................... G01N 21/64  
USPC .................... 250/458.1, 208.2, 216  
See application file for complete search history.

(56) References Cited

U.S. PATENT DOCUMENTS

2005/0162648 A1* 7/2005 Auer et al. .................. 356/318  
2008/0277595 A1* 11/2008 Lundquist et al. ......... 250/458.1

FOREIGN PATENT DOCUMENTS

| JP | 04-369467 A | 12/1992 |
| JP | 2002-526773 A | 8/2002 |
| JP | 2006-322707 A | 11/2006 |
| JP | 2007-212171 A | 8/2007 |
| JP | 4106626 B2 | 4/2008 |
| KR | 10-2008-0105884 A | 12/2008 |
| WO | 03/067230 | 8/2003 |

* cited by examiner

*Primary Examiner* — David Porta  
*Assistant Examiner* — Faye Boosalis  
(74) *Attorney, Agent, or Firm* — Leydig, Voit & Mayer, Ltd.

(57) ABSTRACT

A fluorescence detection optical system detects fluorescence beams with two or more different wavelengths and maintains a focal position through an automatic focusing function. A multi-channel fluorescence detection apparatus includes the fluorescence detection optical system. The fluorescence detection optical system includes an automatic focusing unit which receives light reflected off a microfluidic device and determines a focal point by using an astigmatic method or a knife edge method, and an actuator which adjusts a position of an objective lens according to control of the automatic focusing unit. In addition, the fluorescence detection optical system may include a plurality of dual band pass filters, dichroic devices, etc., which provide light beams emitted from at least two light sources and transfer fluorescence generated from the microfluidic device to a photodetector.

22 Claims, 9 Drawing Sheets

FLUORESCENCE DETECTING OPTICAL SYSTEM AND MULTI-CHANNEL FLUORESCENCE DETECTION APPARATUS INCLUDING THE SAME

CROSS-REFERENCE TO RELATED APPLICATIONS

This application claims priority to Korean Patent Application No. 10-2011-0041994, filed on May 3, 2011, and all the benefits accruing therefrom under 35 U.S.C. §119, the disclosure of which is incorporated herein in its entirety by reference.

BACKGROUND

1. Field

Provided is a fluorescence detection optical system and a multi-channel fluorescence detection apparatus including the same, and more particularly, a fluorescence detection optical system for detecting fluorescence beams with two or more different wavelengths, and for maintaining a constant focal point through an automatic focusing function, and a multi-channel fluorescence detection apparatus including the fluorescence detection optical system.

2. Description of the Related Art

In accordance with the advent of point of care diagnosis, various medical experiments such as gene analysis, external diagnosis, and nucleic acid sequence analysis, for example, have become important, and demand therefor has been increasing. Accordingly, platforms and systems for expediting a substantially large amount of experiments using a substantially small amount of samples have been developed and released. To meet such demand, microfluidic device platforms, such as a microfluidic chip or a lab-on-a-chip ("LOC"), are receiving attention. Microfluidic devices include a plurality of microfluids and microchambers that are designed to control and manipulate a substantially small amount of fluids. Microfluidic devices substantially minimize a reaction time of microfluids. Simultaneously, microfluidic devices react microfluids, and measure reaction results. Microfluidic devices may be manufactured using various methods, and may be formed of various materials according to manufacturing methods.

During gene analysis, for example, to accurately determine whether a sample includes a specific biological material, such as deoxyribonucleic acid ("DNA"), or an amount of the specific DNA, a process of refining/extracting a real biological sample and sufficiently amplifying the refined/extracted sample is needed. Polymerase chain reaction ("PCR") is most widely used among various methods of amplifying a gene. A fluorescence detection method is mainly used to detect DNA amplified through PCR. For example, quantitative real-time PCR ("qPCR") uses a plurality of fluorescent dyes/probes and primer sets to amplify a target biological sample and detect/measure the amplified target sample in real time. For example, qPCR uses a fluorescence characteristic by cutting a TaqMan® probe from a template during DNA amplification. More specifically, as a PCR cycle develops, a number of TaqMan® probes cut from templates exponentially increases, and thus a fluorescence signal level exponentially increases. Such an increase in the fluorescence signal level is measured using an optical system, which enables determination of whether the target sample includes certain DNA or enables performance of quantitative analysis. As the PCR cycle develops, the fluorescence signal level forms an S-curve. A threshold cycle ("Ct") value is set at a point where the fluorescence signal level rapidly changes and the fluorescence signal level is measured thereat. Platforms to which qPCR is applied have been commercially used in various experimental analyses such as external diagnosis, gene analysis, development of a biomarker, and nucleic acid sequence analysis.

A fluorescence detection optical system measures a fluorescence signal level or a change of the fluorescence signal level according to a bio reaction that occurs in a microfluidic device such as a microfluidic chip or a PCR chip. When the fluorescence detection optical system is designed and manufactured, it needs to be considered that a depth of a microchamber of the microfluidic device is merely between several micrometers (μm) and several millimeters (mm). Accordingly, a shape of the microchamber is close to that of a two-dimensional ("2D") chamber since the microchamber has a substantially small depth compared to its width and its length. This means that a range of a focal depth at which a focal point is formed in the microchamber is quite narrow. In particular, when a numerical aperture ("NA") of an objective lens of the fluorescence detection optical system is increased in order to accurately detect fluorescence, the focal depth is further reduced, for example, to several micrometers (μm). Thus, there is a need for precise position-control and precise horizontal-control on the level of several micrometer (μm) between a fluorescence detection optical system and a microfluidic device. If such controls are not precise, focal points formed between chambers in the microfluidic device are formed differently, and thus it is difficult to uniformly and accurately detect fluorescence. Also, if the microfluidic device is attached to or detached from the fluorescence detection optical system, the fluorescence detection optical system needs to maintain its accuracy, and thus a mechanism for attaching or detaching the microfluidic device needs to be precise and thus is complicated, which increases a volume and manufacturing cost of the fluorescence detection optical system.

SUMMARY

Provided are fluorescence detection optical systems that maintain a focal position through an automatic focusing function so as to automatically form focuses in chambers in a microfluidic device even if the microfluidic device is not accurately positioned.

Provided are fluorescence detection optical systems for detecting fluorescence beams with two or more different wavelengths.

Provided are multi-channel fluorescence detection apparatuses including the above-described fluorescence detection optical systems.

Additional aspects will be set forth in part in the description which follows and, in part, will be apparent from the description, or may be learned by practice of the presented embodiments.

Provided is a fluorescence detection optical system including a light source unit which emits excitation light; an objective lens which focuses the excitation light on a microfluidic device; a fluorescence detector which detects fluorescence which is generated by the microfluidic device while a sample in the microfluidic device is excited by the excitation light; an automatic focusing unit which detects the excitation light reflected off the microfluidic device, calculates a focusing error of the excitation light reflected off the microfluidic device, and adjusts a focusing position of the objective lens; and a light transferring unit which transfers the excitation light emitted from the light source unit, transfers the excitation light reflected off the microfluidic device to the automatic focusing unit, and transfers the fluorescence generated by the microfluidic device to the fluorescence detector.

The automatic focusing unit may include a divided-type photodetector that is divided into a plurality of photodetecting segments; a focusing lens which focuses the excitation light reflected off the microfluidic device; an actuator which adjusts the focusing position of the objective lens; and a focusing control unit which calculates the focusing error from an output of the divided-type photodetector and controls an operation of the actuator.

The focusing lens may be an astigmatic lens, and the divided-type photodetector may be a quad-type photodetector including four photodetecting segments.

The automatic focusing unit may further include a knife edge that is disposed between the focusing lens and the divided-type photodetector and blocks light that is out of focus. The divided-type photodetector may be a dual-type photodetector including two photodetecting segments.

The fluorescence detection optical system may further include a diffraction grating that is disposed between the light source unit and the objective lens, and divides the excitation light into a plurality of light beams that are incident on different positions of the microfluidic device.

The light source unit may include a first light source which emits an excitation light beam of a first wavelength; a first excitation light filter which passes the excitation light beam of the first wavelength; a second light source which emits an excitation light beam of a second wavelength that is different from the first wavelength; and a second excitation light filter which passes the excitation light beam of the second wavelength.

The first excitation light filter and the second excitation light filter may be the same dual band pass filter. The band pass filter passes both a light beam of a first wavelength band and a light beam of a second wavelength band.

The light transferring unit may include a first dichroic filter that faces the first light source and the second light source, passes the excitation light beam of the first wavelength emitted from the first light source, and reflects the excitation light beam of the second wavelength emitted from the second light source; a second dichroic filter that is disposed between the objective lens and the fluorescence detector, reflects the excitation light, and passes the fluorescence generated by the microfluidic device; and a beam splitter that is disposed between the first dichroic filter and the second dichroic filter, passes a portion of the excitation light incident on the beam splitter, and reflects a remaining portion of the excitation light incident on the beam splitter.

The second dichroic filter may be a dual band pass dichroic filter that reflects the excitation light beams of the first and the second wavelengths and passes fluorescence beams with third and fourth wavelengths generated by the microfluidic device.

The fluorescence detection optical system may further include a monitoring photodetector which measures an amount of the excitation light that passes from the first dichroic filter through the beam splitter.

The automatic focusing unit may be disposed so as to receive the excitation light that is reflected off the second dichroic filter and then transmitted through the beam splitter.

The fluorescence detector may be disposed so as to detect the fluorescence generated by the microfluidic device and transmitted through the second dichroic filter. The fluorescence detector may include a fluorescence filter which passes only fluorescence beams from among light transmitted from the second dichroic filter; and a fluorescence photodetector which detects the fluorescence beams transmitted through the fluorescence filter.

The fluorescence filter may be a dual band pass filter that passes only the fluorescence beams with a third wavelength and the fluorescence beams with a fourth wavelength generated by the microfluidic device.

The fluorescence detection optical system may further include a plurality of fluorescence detectors. A first fluorescence detector detects the fluorescence beams with the third wavelength from among light transmitted through the second dichroic filter; and a second fluorescence detector detects the fluorescence beams with the fourth wavelength from among the light transmitted through the second dichroic filter. The light transferring unit further includes a third dichroic filter that passes and transfers the fluorescence beams with the third wavelength from among the light transmitted through the second dichroic filter to the first fluorescence detector and reflects and transfers the fluorescence beams with the fourth wavelength to the second fluorescence detector.

The first fluorescence detector may include a first fluorescence filter which passes the fluorescence beams with the third wavelength from among the light emitted through the third dichroic filter; and a first fluorescence photodetector which detects the fluorescence beams transmitted through the first fluorescence filter.

The second fluorescence detector may include a second fluorescence filter which passes the fluorescence beams with the fourth wavelength from among light reflected by the third dichroic filter; and a second fluorescence photodetector which detects the fluorescence beams transmitted through the second fluorescence filter.

The first fluorescence filter and the second fluorescence filter may be the same dual band pass filter. The dual band pass filter passes both the fluorescence beams with the third wavelength and the fluorescence beams with the fourth wavelength.

The light source unit may include a first light source which emits an excitation light beam of a first wavelength and a second light source which emits an excitation light of a second wavelength that is different from the first wavelength.

The fluorescence detection optical system may further include a plurality of fluorescence detectors and a plurality of automatic focusing unites. A first fluorescence detector detects a fluorescence beam with a third wavelength that is generated while the sample is excited by the excitation light beam of the first wavelength, and a second fluorescence detector detects a fluorescence beam with a fourth wavelength that is generated while a sample is excited by the excitation light beam of the second wavelength. A first automatic focusing unit measures the excitation light beam of the first wavelength reflected off the microfluidic device and performs an automatic focusing function, and a second automatic focusing unit measures the excitation light beam of the second wavelength reflected off the microfluidic device and performs an automatic focusing function.

The light transferring unit transfers the excitation light beam of the first wavelength and the excitation light beam of the second wavelength to the microfluidic device, transfers the fluorescence beam with the third wavelength and the fluorescence beam with the fourth wavelength to the first fluorescence detector and the second fluorescence, respectively, and transfers the excitation light beam of the first wavelength and the excitation light beam of the second wavelength reflected off the microfluidic device, to the first automatic focusing unit and the second automatic focusing unit, respectively.

The light transferring unit may include a first dichroic filter that faces the first light source and the first fluorescence detector, reflects the excitation light beam of the first wavelength, and passes and provides the fluorescence beam with the third wavelength to the first fluorescence detector; a second dichroic filter that faces the second light source and the second fluorescence detector, reflects the excitation light beam of the second wavelength, and passes and provides the fluorescence beam with the fourth wavelength to the second fluorescence detector; a first beam splitter that is disposed between the first light source and the first dichroic filter, passes a portion of the excitation light beam of the first wavelength incident on the first beam splitter, and reflects a remaining portion of the excitation light beam of the first wavelength; a second beam splitter that is disposed between the second light source and the second dichroic filter, passes a portion of the excitation light beam of the second wavelength incident on the second beam splitter, and reflects a remaining portion of the excitation light beam of the second wavelength; and a third dichroic filter that faces the first dichroic filter and the second dichroic filter, reflects the excitation light beam of the first wavelength and the fluorescence beam with the third wavelength, and passes the excitation light beam of the second wavelength and the fluorescence beam with the fourth wavelength.

The fluorescence detection optical system may further include a first monitoring photodetector which measures an amount of the excitation light beam of the first wavelength reflected by the first beam splitter from the first light source, and a second monitoring photodetector which measures an amount of the excitation light beam of the second wavelength reflected by the second beam splitter from the second light source.

The first automatic focusing unit may be disposed so as to receive the excitation light beam of the first wavelength reflected by the first dichroic filter and then reflected by the first beam splitter toward the first automatic focusing unit, and the second automatic focusing unit may be disposed so as to receive the excitation light beam of the second wavelength reflected by the second dichroic filter and then reflected by the second beam splitter toward the second automatic focusing unit.

The first automatic focusing unit may include a first divided-type photodetector that is divided into a plurality of photodetecting segments and a first focusing lens which focuses the excitation light beam of the first wavelength reflected off the microfluidic device, and the second automatic focusing unit may include a second divided-type photodetector that is divided into a plurality of photodetecting segments and a second focusing lens which focuses the excitation light beam of the second wavelength reflected off the microfluidic device.

The first automatic focusing unit and the second automatic focusing unit may share an actuator which adjusts the focusing position of the objective lens; and a focusing controller which calculates a focusing error of the excitation light beam of the first wavelength and a focusing error of the excitation light beam of the second wavelength, from outputs from the first divided-type photodetector and the second divided-type photodetector, and controls an operation of the actuator.

Provided is a fluorescence detection apparatus including at least one fluorescence detection optical system; and a moving member which moves the at least one fluorescence detection optical system.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
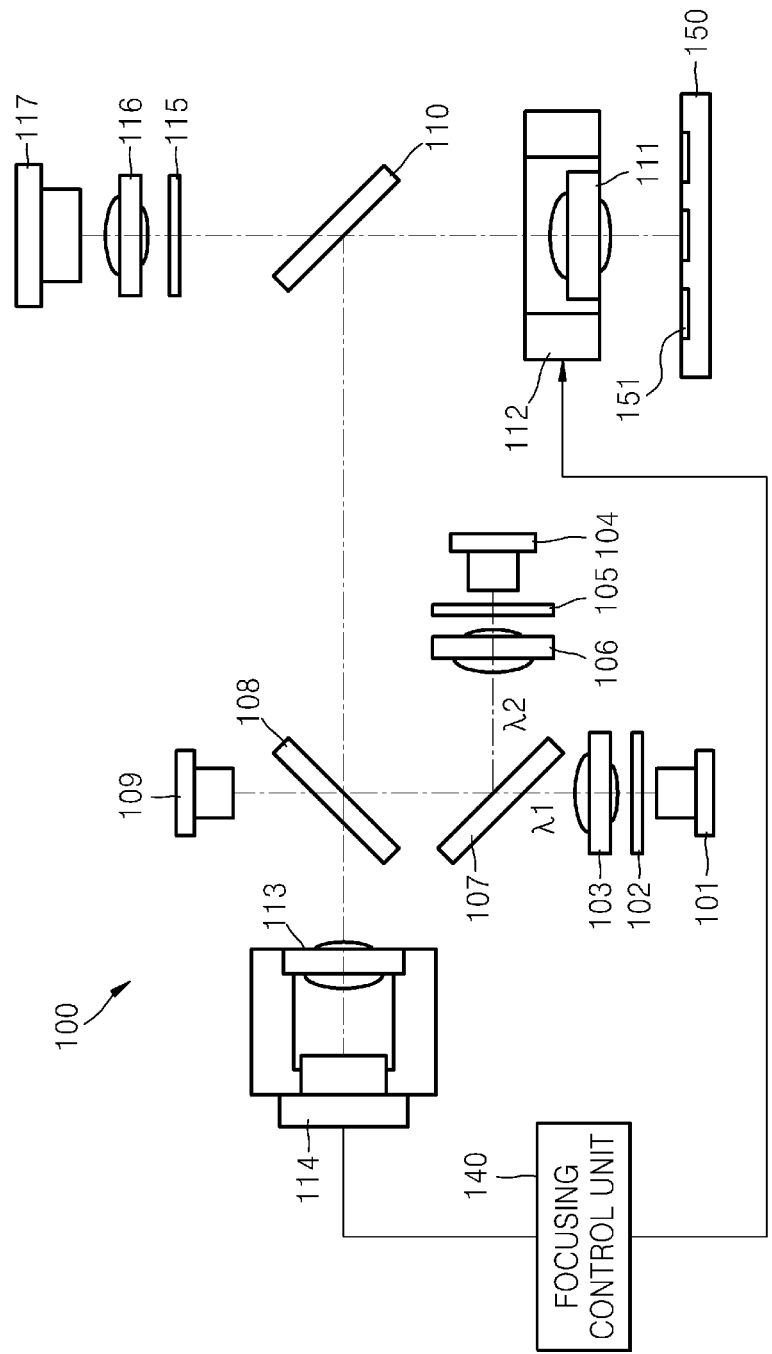
FIG. 1 is a schematic view of a fluorescence detection optical system, according to an embodiment of the present invention.

Reference will now be made in detail to embodiments, examples of which are illustrated in the accompanying drawings, wherein like reference numerals refer to like elements throughout. In this regard, the embodiments may have different forms and should not be construed as being limited to the descriptions set forth herein. Accordingly, the embodiments are merely described below, by referring to the figures, to explain aspects of the present description.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

FIG. 1 is a schematic view of a fluorescence detection optical system 100 according to an embodiment of the present invention. Referring to FIG. 1, the fluorescence detection optical system 100 may include a first light source 101 for emitting an excitation light beam of a first wavelength $\lambda_1$, a first excitation light filter 102 for passing the excitation light beam of the first wavelength $\lambda 1$ only, a first collimating lens 103 for converting the excitation light beam of the first wavelength $\lambda 1$ into a parallel beam, a second light source 104 for emitting an excitation light beam of a second wavelength $\lambda 2$, a second excitation light filter 105 for passing the excitation light beam of the second wavelength $\lambda 2$ only, a second collimating lens 106 for converting the excitation light beam of the second wavelength $\lambda 2$ into a parallel beam, a first dichroic filter 107 for passing the excitation light beam of the first wavelength $\lambda 1$ and reflecting the excitation light beam of the second wavelength $\lambda 2$, a beam splitter 108 for passing a portion of an incident light beam and reflecting the remaining portion of the incident light beam, a monitoring photodetector 109 for measuring amounts of excitation light beams passed through the beam splitter 108, a second dichroic filter 110 for reflecting excitation light beams and passing fluorescence generated by a microfluidic device 150, an objective lens 111 for focusing excitation light beams in a chamber 151 of the microfluidic device 150, an actuator 112 for adjusting a focusing position of the objective lens 111, a fluorescence filter 115 for passing only fluorescence from among light beams passed through the second dichroic filter 110, a fluorescence photodetector 117 for detecting the fluorescence passed through the fluorescence filter 115, a first focusing lens 116 disposed between the fluorescence filter 115 and the fluorescence photodetector 117 and for focusing fluorescence on the fluorescence photodetector 117, a second focusing lens 113 for focusing excitation light beams reflected off the microfluidic device 150, a divided-type photodetector 114 for detecting the excitation light beams reflected off the microfluidic device 150, and a focusing control unit 140 for calculating a focusing error from an output from the divided-type photodetector 114 and for controlling an operation of the actuator 112.

From among the above-described components, the first light source 101, the first excitation light filter 102, the first collimating lens 103, the second light source 104, the second excitation light filter 105, and the second collimating lens 106 constitute a light source unit. The light source unit may include the monitoring photodetector 109. The light source unit may provide excitation light beams of different first and second wavelengths $\lambda 1$ and $\lambda 2$ by using the first and second light sources 101 and 104. In an embodiment, for example, the first and second light sources 101 and 104, which emit light beams having different wavelengths, may be light emitting diodes ("LEDs"), laser diodes ("LDs"), or halogen lamps. Wavelengths of the light beams emitted from the first and second light sources 101 and 104 may be selected from wavelengths of cyan, amber, and red light beams. In particular, in order to minimize cross talk, the wavelengths of the light beams emitted from the first and second light sources 101 and 104 may be selected such that a wavelength band of the first light source 101 and a wavelength band of the second light source 104 do not overlap each other. In one embodiment, for example, if the first light source 101 is an LED for emitting a cyan light beam, the second light source 104 may be an LED for emitting a green light beam. In addition, if the first light source 101 is an LED for emitting an amber light beam, the second light source 104 may be an LED for emitting a red light beam.

The first excitation light filter 102 may be a band pass filter that passes only a light beam of a first wavelength band. The second excitation light filter 105 may be a band pass filter that passes only a light beam of a second wavelength band. However, in order to reduce a number of components and easily perform assembly, the first excitation light filter 102 and the second excitation light filter 105 may be the same filter. In one embodiment, for example, both the first excitation light filter 102 and the second excitation light filter 105 may each be a dual band pass filter that passes both the light beams of the first wavelength band and light beams of the second wavelength band.

In addition, the first dichroic filter 107, the beam splitter 108, and the second dichroic filter 110 constitute a light transferring unit that divides and provides excitation light beams emitted from the first and second light sources 101 and 104 to the monitoring photodetector 109 and the microfluidic device 150, provides excitation light beams reflected off the microfluidic device 150 to the divided-type photodetector 114, and provides fluorescence generated by the chamber 151 of the microfluidic device 150 to the fluorescence photodetector 117.

In one embodiment, for example, the first dichroic filter 107 may pass an excitation light beam of a first wavelength $\lambda 1$ and may reflects an excitation light beam of a second wavelength $\lambda 2$ so that the excitation light beam of the first wavelength $\lambda 1$ and the excitation light beam of the second wavelength $\lambda 2$ may proceed along the same optical path. To achieve this, the first dichroic filter 107 may be angled at about 45 degrees with respect to light paths from the first light source 101 and from the second light source 104. The beam splitter 108 may pass and provide portions (e.g., about 10%) of incident excitation light beams to the monitoring photodetector 109, and may reflect and provide remaining portions (e.g., about 90%) of incident excitation light beams to the microfluidic device 150. In addition, the second dichroic filter 110 may be configured so as to reflect excitation light beams toward the microfluidic device 150 and pass fluorescence generated by the chamber 151 of the microfluidic device 150 toward the fluorescence photodetector 117. In particular, the second dichroic filter 110 may be a dual band pass dichroic filter that reflects the excitation light beams of the first and the second wavelengths $\zeta 1$ and $\lambda 2$ and passes fluorescence beams with third and fourth wavelengths.

The monitoring photodetector 109 measures amounts of excitation light beams transmitted through the beam splitter 108, and may include, for example, a single photodiode. The fluorescence detection optical system 100 may maintain constant outputs of the first and second light sources 101 and 104, with reference to the amounts of the excitation light beams transmitted through the beam splitter 108, which are measured by the monitoring photodetector 109. In FIG. 1, the monitoring photodetector 109 measures the amounts of the excitation light beams transmitted through the beam splitter 108, but the present invention is not limited to this. In an alternative embodiment, for example, the monitoring photodetector 109 may be disposed so as to measure excitation light beams reflected off the beam splitter 108. In this case, excitation light beams transmitted through the beam splitter 108 may be transmitted to the microfluidic device 150. In this alternative case, transmittance and reflectance of the beam splitter 108 may be about 90% and about 10%, respectively.

In addition, the fluorescence filter 115, the first focusing lens 116, and the fluorescence photodetector 117 constitute a fluorescence detector that detects fluorescence generated by the chamber 151 of the microfluidic device 150. The fluorescence filter 115 blocks light that is not fluorescence so that light that is not fluorescence may not reach the fluorescence photodetector 117. In one embodiment, for example, the fluorescence filter 115 may be a dual band pass filter that passes only a fluorescence beam with a third wavelength generated while a sample in the chamber 151 is excited by the excitation light beam of the first wavelength $\lambda 1$, and a fluorescence beam with a fourth wavelength generated while the sample in the chamber 151 is excited by the excitation light beam of the second wavelength $\lambda 2$. The fluorescence photodetector 117 may be, for example, a photodiode array, a photo multiplier tube ("PMT"), a charge coupled device ("CCD") image sensor, a complementary metal oxide semiconductor ("CMOS") image sensor, an avalanche photodiode ("APD"), or the like.

The actuator 112, the second focusing lens 113, the divided-type photodetector 114, and the focusing control unit 140 constitute an automatic focusing unit. The second focusing lens 113 focuses excitation light beams reflected off the microfluidic device 150 towards the divided-type photodetector 114. The divided-type photodetector 114 may be divided into a plurality of photodetecting segments and may measure amounts of light beams that are incident on the photodetecting segments, respectively. Then, the focusing control unit 140 may calculate a focusing error from an output from the divided-type photodetector 114, and may control an operation of the actuator 112. The automatic focusing unit calculates the focusing error and adjusts a focus by using an astigmatic method or a knife edge method.

Figure 2A:
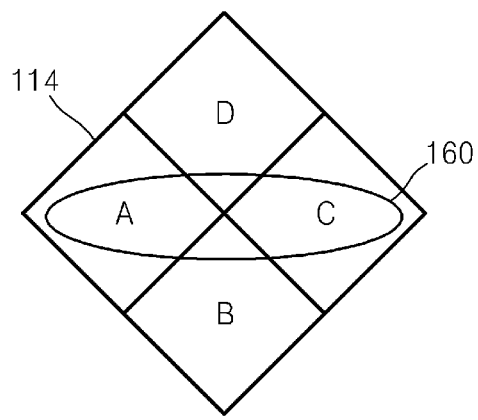
FIGS. 2A through 2C are diagrams for explaining a principle of adjusting a focus by using an astigmatic method, according to an embodiment of the present invention.
Figure 2B:
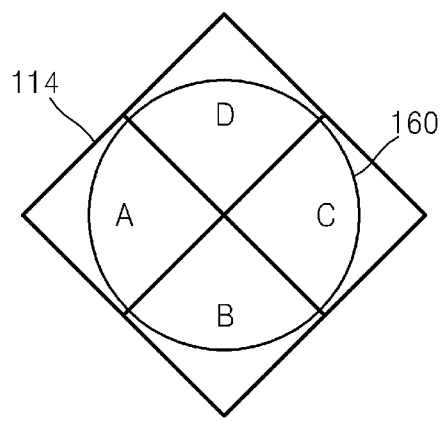
Figure 2C:
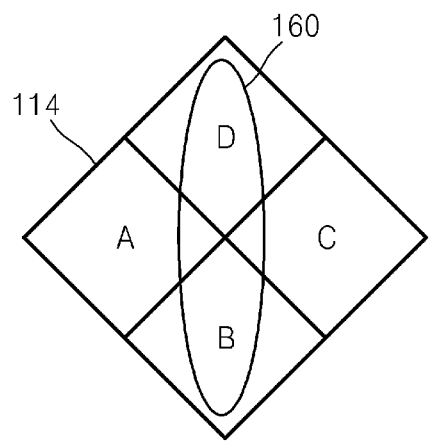

FIGS. 2A through 2C are diagrams for explaining a principle of adjusting a focus by using an astigmatic method, according to an embodiment of the present invention. In the astigmatic method, the second focusing lens 113 may be an astigmatic lens, and the divided-type photodetector 114 may use a 4-split type photodetector that is divided into four segments A through D. If the objective lens 111 is relatively close to the chamber 151 of the microfluidic device 150, an optical spot 160 formed on the divided-type photodetector 114 by the second focusing lens 113 is lengthened in a horizontal direction, as shown in FIG. 2A. Thus, a total amount (A+C) of light beams measured in a first segment A and a third segment C is greater than a total amount (B+D) of light beams measured in a second segment B and a fourth segment D. When A+C>B+D, the focusing control unit 140 operates the actuator 112 to move the objective lens 111 away from the chamber 151 of the microfluidic device 150. The actuator 112 may be, for example, a voice coil motor ("VCM").

In contrast, when excitation light beams are correctly focused in the chamber 151 of the microfluidic device 150, the optical spot 160 formed on the divided-type photodetector 114 by the second focusing lens 113 may have a perfectly circular shape, as shown in FIG. 2B. Thus, A+C=B+D. In this case, the focusing control unit 140 does not have to adjust a location of the objective lens 111.

When the objective lens 111 is relatively far from the chamber 151 of the microfluidic device 150, the optical spot 160 formed on the divided-type photodetector 114 by the second focusing lens 113 is lengthened in a vertical direction, as shown in FIG. 2C. Thus, a total amount A+C of light beams measured in the first segment A and the third segment C is smaller than a total amount (B+D) measured in the second segment B and the fourth segment D. When A+C<B+D, the focusing control unit 140 operates the actuator 112 to move the objective lens 111 toward the chamber 151 of the microfluidic device 150.

Figure 3A:
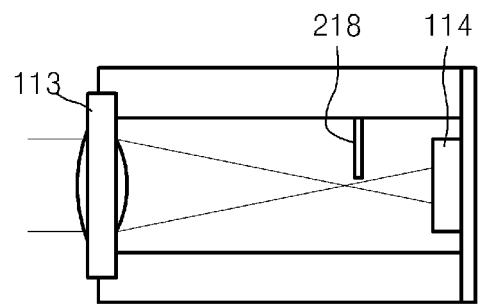
FIGS. 3A through 5B are diagrams for explaining a principle of adjusting a focus by using a knife edge method, according to an embodiment of the present invention.
Figure 3B:
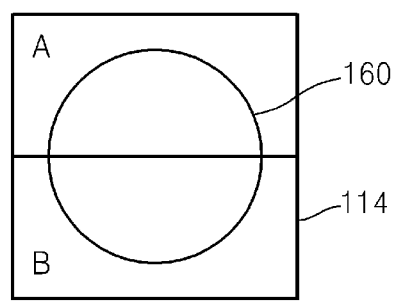

FIGS. 3A through 5B are diagrams for explaining a principle of adjusting a focus by using a knife edge method, according to an embodiment of the present invention. In the knife edge method, the second focusing lens 113 may use a general convex lens. The divided-type photodetector 114 may use a dual-type photodetector that is divided into two segments A and B. In addition, a knife edge 218 that blocks light that is out of focus is disposed between the second focusing lens 113 and the divided-type photodetector 114. When excitation light beams are correctly focused in the chamber 151 of the microfluidic device 150, a diameter of a light beam focused by the second focusing lens 113 is minimized at a position of the knife edge 218, as shown in FIG. 3A. Thus, since light is not blocked by the knife edge 218, optical amounts measured in a first segment A and a second segment B are the same, as shown in FIG. 3B (A=B).

Figure 4A:
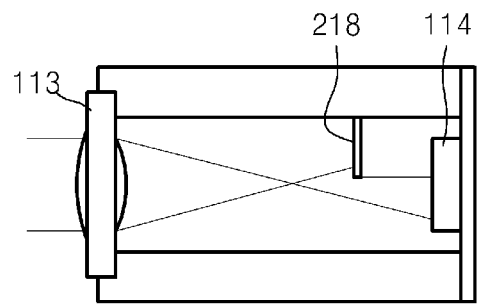
Figure 4B:
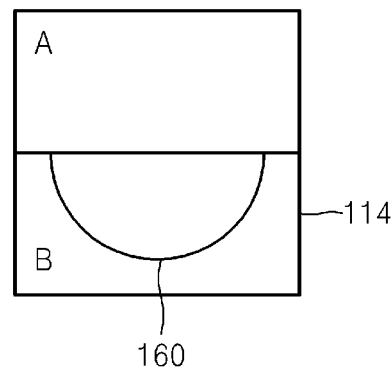
Figure 5A:
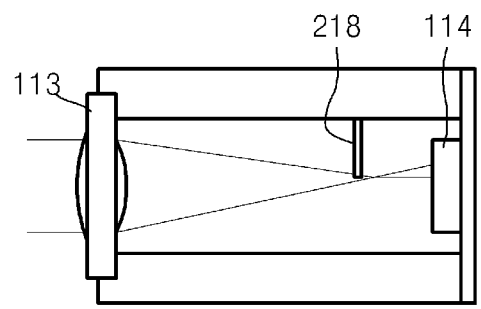
Figure 5B:
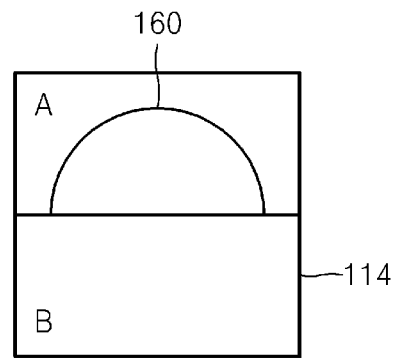

In contrast, when the objective lens 111 is relatively close to the chamber 151 of the microfluidic device 150, a diameter of a light beam focused by the second focusing lens 113 is minimized in front of the knife edge 218, as shown in FIG. 4A. Thus, as shown in FIG. 4B, since light that proceeds towards the first segment A is partially blocked, an optical amount measured in the first segment A is less than an optical amount measured in the second segment B (A<B). When the objective lens 111 is relatively far from the chamber 151 of the microfluidic device 150, a diameter of a light beam focused by the second focusing lens 113 is minimized past the knife edge 218, as shown in FIG. 5A. Thus, as shown in FIG. 5B, since light that proceeds towards the second segment B is partially blocked, an optical amount measured in the first segment A is greater than an optical amount measured in the second segment B (A>B). Based on such principles, it may be known when excitation light beams are correctly focused on the chamber 151 of the microfluidic device 150.

Hereinafter, an operation of the fluorescence detection optical system 100 of FIG. 1 will be described. First, the first light source 101 is powered on so as to emit an excitation light beam of a first wavelength $\lambda 1$, and the second light source 104 is powered off so as not to emit any excitation light beam. The excitation light beam of the first wavelength $\lambda 1$ becomes a parallel beam while being transmitted through the first excitation light filter 102 and the first collimating lens 103. In addition, the excitation light beam is transmitted through the first dichroic filter 107 and then is incident on the beam splitter 108. A portion (for example, about 10%) of the excitation light beam is transmitted through the beam splitter 108 and is incident on the monitoring photodetector 109. The monitoring photodetector 109 measures an amount of the excitation light beam. A measurement result of the monitoring photodetector 109 is used to adjust an output of the first light source 101.

The remaining portion (for example, about 90%) of the excitation light beam is reflected off the beam splitter 108 and the second dichroic filter 110, and then is focused in the chamber 151 of the microfluidic device 150 through the objective lens 111. A fluorescence material labeling a sample in the chamber 151 is excited by the excitation light beam so as to generate a fluorescence beam with a third wavelength. Then, the excitation light beam and the fluorescence beam are reflected off the microfluidic device 150 and then are incident on the second dichroic filter 110. In order to reflect the excitation light beam and the fluorescence beam, the microfluidic device 150 may be formed of a reflective material such as silicon. A surface of the microfluidic device 150 may be coated with a reflective material.

The fluorescence beam may be transmitted through the second dichroic filter 110 and then may be incident on the fluorescence photodetector 117 through the fluorescence filter 115 and the first focusing lens 116. Thus, the fluorescence photodetector 117 may detect the fluorescence beam, and a type and an amount of a sample in the chamber 151 may be determined, according to a detection result of the fluorescence photodetector 117. On the other hand, the excitation light beam is reflected off the second dichroic filter 110 and then is incident on the beam splitter 108. A portion of the excitation light beam is transmitted through the beam splitter 108 and then is incident on the divided-type photodetector 114 through the second focusing lens 113. Thus, automatic focusing of the objective lens 111 may be performed by using the above-described astigmatic method or knife edge method. Thus, the excitation light beam may be correctly focused in the chamber 151 of the microfluidic device 150.

When the fluorescence generated by the excitation light beam of the first wavelength $\lambda 1$ is completely detected, the first light source 101 is powered off, and the second light source 104 is powered on. Then, a fluorescence detection operation and an automatic focusing operation may be performed on the excitation light beam of the second wavelength $\lambda 2$. A fluorescence beam with a fourth wavelength generated by the excitation light beam of the second wavelength $\lambda 2$ proceeds along the same path as the fluorescence beam with the third wavelength generated by the excitation light beam of the first wavelength $\lambda 1$, and thus a description thereof will be omitted.

As described above, the fluorescence detection optical system 100 may automatically focus light in the chamber 151 of the microfluidic device 150 by using an automatic focusing function even if the microfluidic device 150 is not precisely disposed. In addition, the fluorescence detection optical system 100 may detect fluorescence beams with different two wavelengths. Thus, when the fluorescence detection optical system 100 is used, a volume and manufacturing cost of a fluorescence detection apparatus for detecting fluorescence beams with a plurality of wavelengths generated by a plurality of chambers may be reduced.

Figure 6:
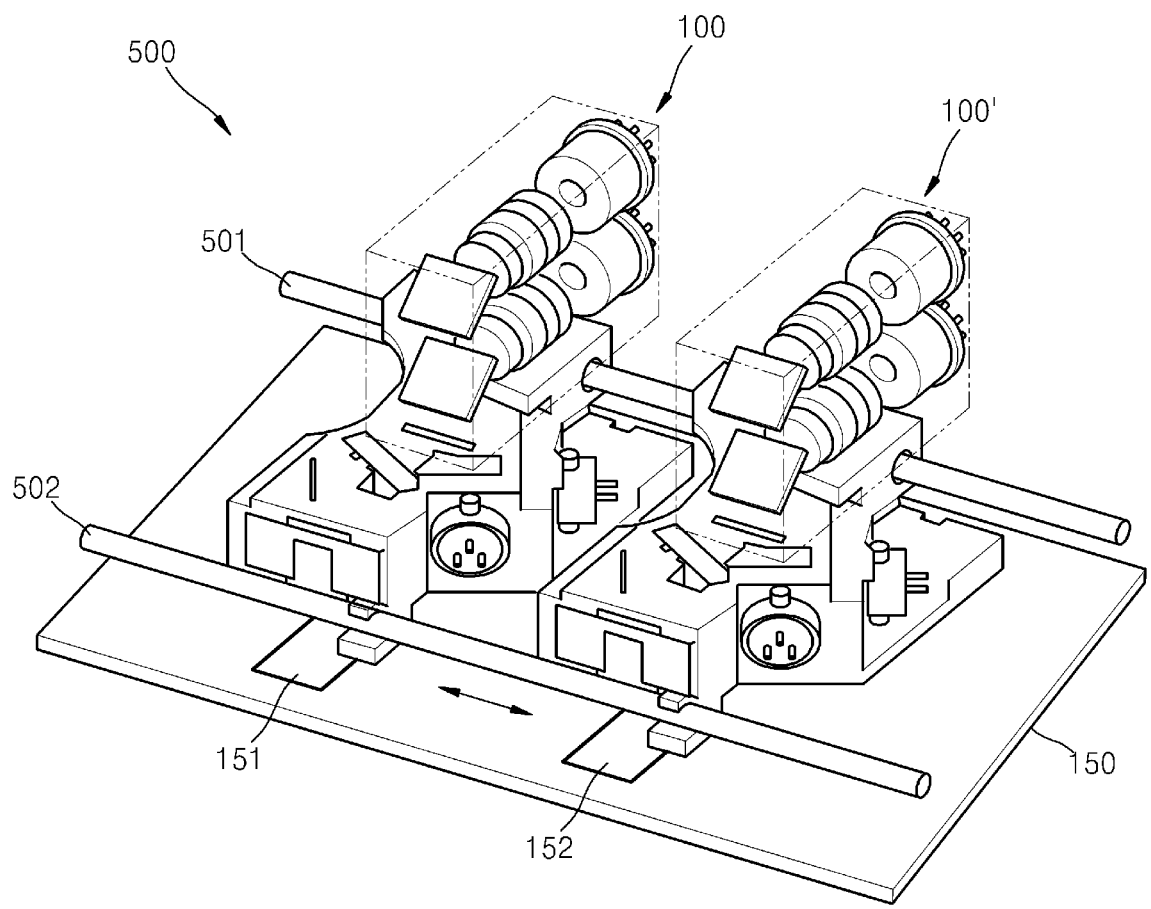
FIG. 6 is a schematic diagram of a multi-channel fluorescence detection apparatus including a fluorescence detection optical system, according to an embodiment of the present invention.

FIG. 6 is a schematic diagram of a multi-channel fluorescence detection apparatus 500 including the fluorescence detection optical system 100, according to an embodiment of the present invention. Referring to FIG. 6, the multi-channel fluorescence detection apparatus 500 may include two fluorescence detection optical systems 100 and 100' for detecting fluorescence by using excitation light beams of different wavelengths. The two fluorescence detection optical systems 100 and 100' may each have the same configuration as that shown in FIG. 1 except for wavelengths of excitation light beams and fluorescence. In embodiments, for example, a first fluorescence detection optical system 100 may be configured to emit excitation light beams of first and second wavelength $\lambda 1$ and $\lambda 2$ so as to detect fluorescence beams with third and fourth wavelengths. A second fluorescence detection optical system 100' may be configured to emit excitation light beams of fifth and sixth wavelengths so as to detect fluorescence beams with seventh and eighth wavelengths. In particular, in order to minimize cross talk and to increase accuracy, the first wavelength $\lambda 1$ and the second wavelength $\lambda 2$ may be selected so as not to overlap each other, and the fifth and sixth wavelengths may be selected so as not to overlap each other. In one embodiment, for example, the first fluorescence detection optical system 100 may emit a cyan excitation light beam and a green excitation light beam, and the second fluorescence detection optical system 100' may emit an amber excitation light beam and a red excitation light beam.

Referring to FIG. 6, the multi-channel fluorescence detection apparatus 500 may further include a lead screw 501 and a guide rail 502 that are moving members for moving the fluorescence detection optical systems 100 and 100' relative to each other and a base. First ends of the fluorescence detection optical systems 100 and 100' are coupled to the lead screw 501, and second ends of the fluorescence detection optical systems 100 and 100' are supported by the guide rail 502. According to this structure, when the lead screw 501 is rotated manually, or mechanically such as by a motor (not shown) connected to the lead screw 501, the fluorescence detection optical systems 100 and 100' may be moved along a direction indicated by an arrow in FIG. 6.

Thus, the fluorescence detection optical systems 100 and 100' may detect fluorescence while sequentially moving over a plurality of chambers 151 and 152 of the microfluidic device 150. In one embodiment, for example, while the first fluorescence detection optical system 100 detects a fluorescence beam generated by an excitation light beam of a first wavelength $\lambda 1$ with respect to a first chamber 151, the second fluorescence detection optical system 100' detects a fluorescence beam generated by an excitation light beam of a fifth wavelength with respect to a second chamber 152. Then, after the fluorescence detection optical systems 100 and 100' are moved in a left direction, the second fluorescence detection optical system 100' may detect a fluorescence beam generated by another excitation light beam of the fifth wavelength with respect to the first chamber 151. Then, when fluorescence generated by the excitation light beams of the first and fifth wavelengths with respect to the first and second chambers 151 and 152 is completely detected, fluorescence generated by excitation light beams of second and sixth wavelengths after the fluorescence detection optical systems 100 and 100' are moved in a right direction, may be detected. Similarly, the multi-channel fluorescence detection apparatus 500 may simultaneously detect fluorescence beams by using a plurality of excitation light beams with respect to the first and second chambers 151 and 152.

Figure 7:
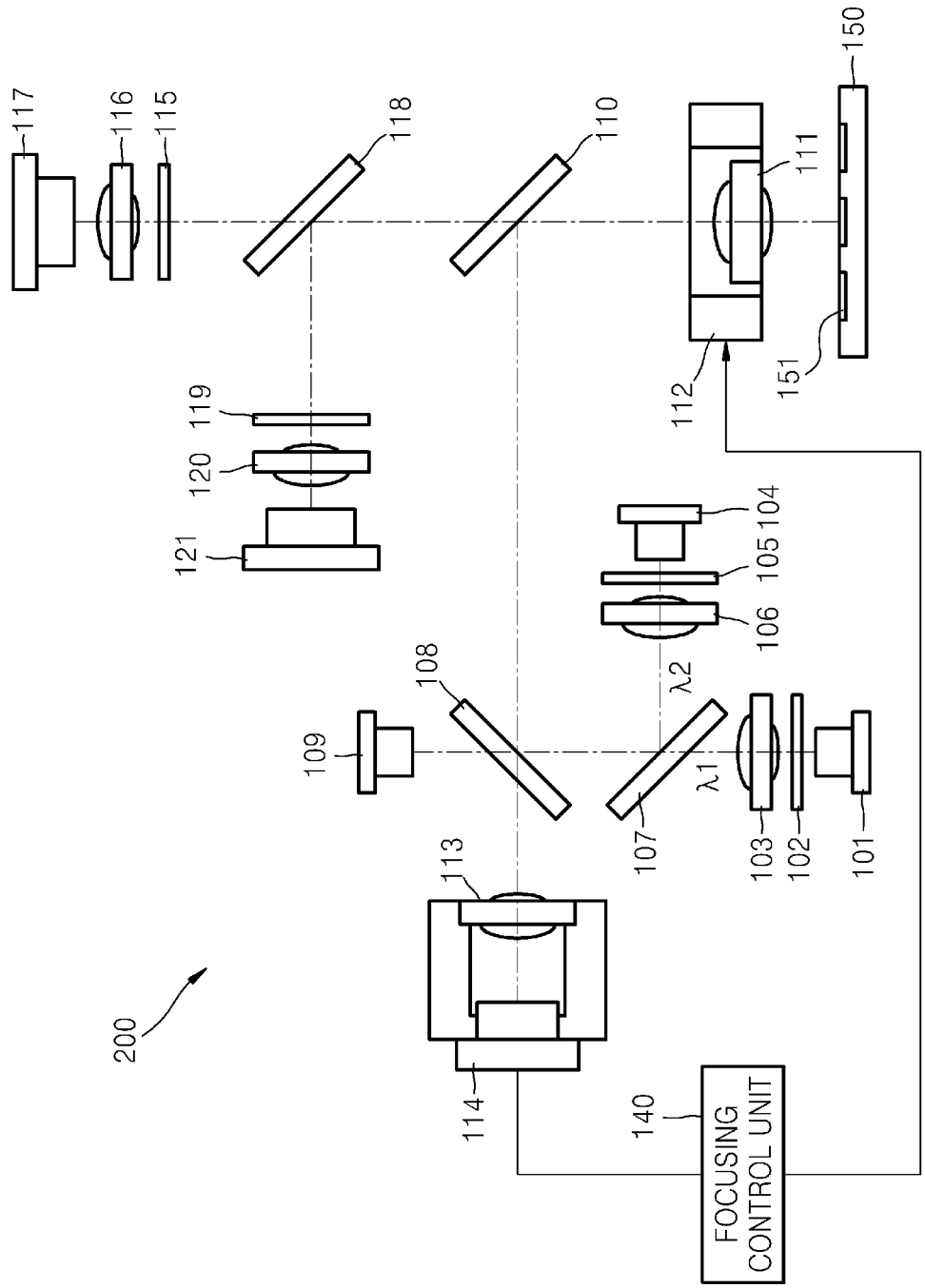
FIG. 7 is a schematic diagram of a fluorescence detection optical system, according to another embodiment of the present invention.

The fluorescence detection optical system 100 of FIG. 1 may detect fluorescence generated by a single excitation light beam at one time, but may be configured to simultaneously detect fluorescence generated by two excitation light beams at one time. FIG. 7 is a schematic diagram of a fluorescence detection optical system 200, according to another embodiment of the present invention. Referring to FIG. 7, the fluorescence detection optical system 200 is different from the fluorescence detection optical system 100 of FIG. 1 in that the fluorescence detection optical system 200 further includes a third dichroic filter 118, a second fluorescence filter 119, a third focusing lens 120, and a second fluorescence photodetector 121, disposed between the second dichroic filter 110 and a first fluorescence filter 115.

In one embodiment, for example, the third dichroic filter 118 may be configured so as to pass a fluorescence beam with a third wavelength and to reflect a fluorescence beam with a fourth wavelength from among fluorescence beams transmitted through the second dichroic filter 110. Thus, a first fluorescence photodetector 117 may detect the fluorescence beam with the third wavelength only, and the second fluorescence photodetector 121 may detect the fluorescence beam with the fourth wavelength. That is, according to the illustrated embodiment, a first fluorescence filter 115, the first focusing lens 116, and the first fluorescence photodetector 117 constitute a first fluorescence detector for detecting the fluorescence beam with the third wavelength. The second fluorescence filter 119, the third focusing lens 120, and the second fluorescence photodetector 121 constitute a second fluorescence detector for detecting the fluorescence beam with the fourth wavelength. In this case, the first fluorescence filter 115 may be a band pass filter that passes the fluorescence beam with the third wavelength only. The second fluorescence filter 119 may be a band pass filter that passes the fluorescence beam with the fourth wavelength only. However, in order to reduce a number of components and easily perform assembly, the first fluorescence filter 115 and the second fluorescence filter 119 may be the same band pass filter. In one embodiment, for example, the first fluorescence filter 115 and the second fluorescence filter 119 may each be a dual band pass filter that passes both the fluorescence beam with the third wavelength and the fluorescence beam with the fourth wavelength.

Since the fluorescence detection optical system 200 of FIG. 7 includes two fluorescence detectors, the first light source 101 and the second light source 104 may simultaneously emit excitation light beams, and fluorescence beams with two wavelengths may be detected. The fluorescence detection optical system 200 may also be used in the multi-channel fluorescence detection apparatus 500 of FIG. 6. In one embodiment, for example, when two fluorescence detection optical systems 200 are disposed in parallel to each other in the multi-channel fluorescence detection apparatus 500, the multi-channel fluorescence detection apparatus 500 may detect fluorescence beams with four wavelengths while the two fluorescence detection optical systems 200 are scanned in one direction.

Figure 8:
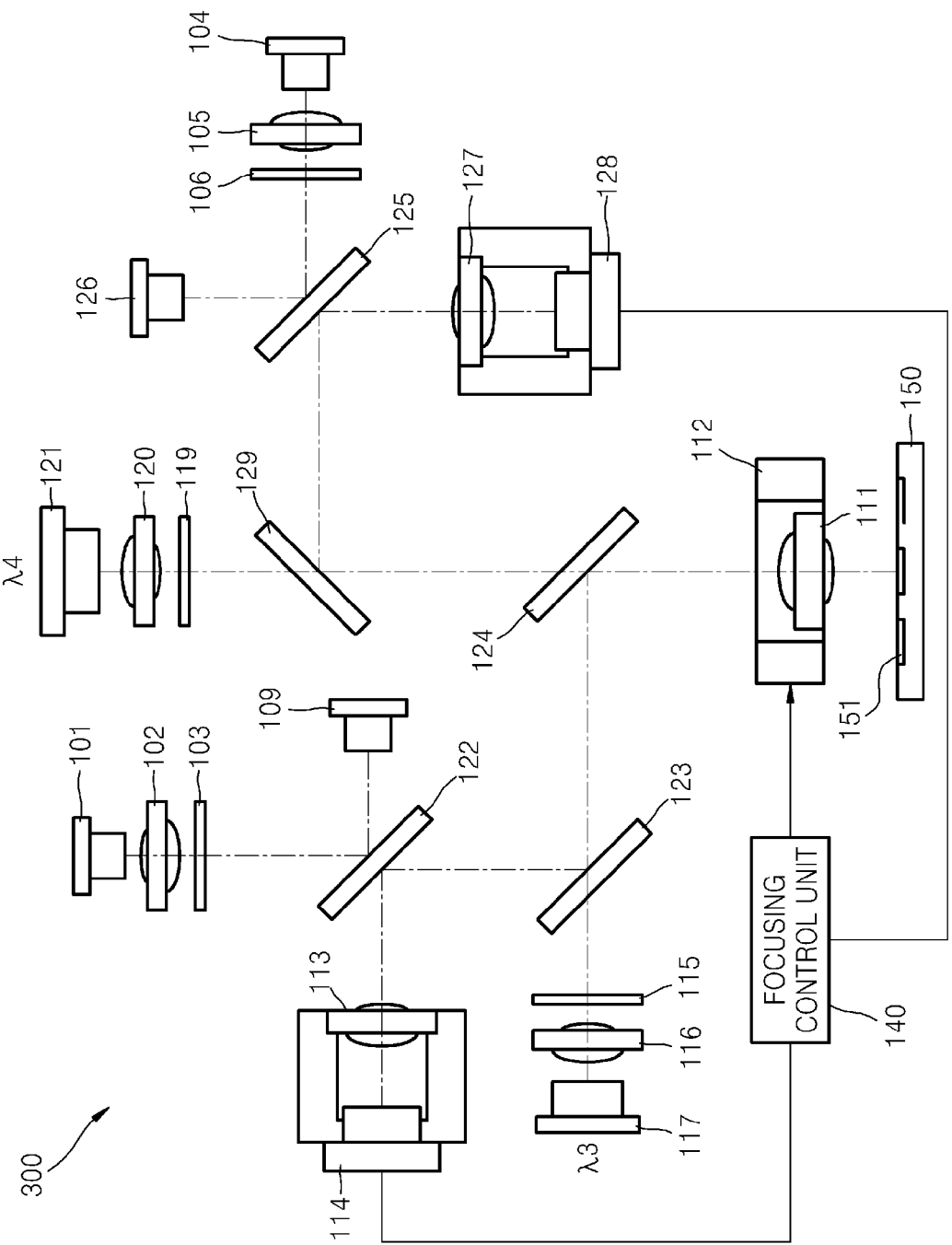
FIG. 8 is a schematic diagram of a fluorescence detection optical system, according to another embodiment of the present invention.

In addition, the fluorescence detection optical systems 100 and 200 of FIGS. 1 and 7 may perform an automatic focusing operation with respect to excitation light beams of two wavelengths by using a single common automatic focusing unit. However, separate automatic focusing units may be used for different excitation light beams. FIG. 8 is a schematic diagram of a fluorescence detection optical system 300 according to another embodiment of the present invention. Referring to FIG. 8, the fluorescence detection optical system 300 may include a first light source unit 101, 102, 103, and 109 for emitting an excitation light beam of a first wavelength λ1, a second light source unit 104, 105, 106, and 126 for emitting an excitation light beam of a second wavelength λ2, a first fluorescence detection unit 115, 116, and 117 for detecting a fluorescence beam with a third wavelength generated while a sample in the chamber 151 is excited by the excitation light beam of the first wavelength λ1, a second fluorescence detection unit 119, 120, and 121 for detecting a fluorescence beam with a fourth wavelength generated while the sample in the chamber 151 is excited by the excitation light beam of the second wavelength λ2, a first automatic focusing unit 112, 113, 114, and 140 that measures the excitation light beam of the first wavelength λ1 reflected off the microfluidic device 150 so as to perform an automatic focusing function, a second automatic focusing unit 112, 127, 128, and 140 that measures the excitation light beam of the second wavelength λ2 reflected off the microfluidic device 150 so as to perform an automatic focusing function, a light transferring unit 122, 123, 124, 125, and 129 for transferring the excitation light beam of the first wavelength λ1 and the excitation light beam of the second wavelength λ2 to the microfluidic device 150, for transferring the fluorescence beam with the third wavelength and the fluorescence beam with the fourth wavelength, which are generated by the microfluidic device 150, to the first fluorescence detection unit 115, 116, and 117 and the second fluorescence detection unit 119, 120, and 121, respectively, and for transferring the excitation light beam of the first wavelength λ1 and the excitation light beam of the second wavelength λ2 reflected off the microfluidic device 150 to the first automatic focusing unit 112, 113, 114, and 140 and the second automatic focusing unit 112, 127, 128, and 140, respectively, and the objective lens 111 for focusing the excitation light beams of the first and second wavelength λ1 and λ2 in the chamber 151 of the microfluidic device 150.

The first light source unit 101, 102, 103, and 109 may include the first light source 101 for emitting an excitation light beam of a first wavelength λ1, the first excitation light filter 102 for passing the excitation light beam of the first wavelength λ1 only, the first collimating lens 103 for converting the excitation light beam of the first wavelength λ1 into a parallel beam, and a first monitoring photodetector 109 for measuring an amount of the excitation light beam of the first wavelength λ1. In addition, the second light source unit 104, 105, 106, and 126 may include the second light source 104 for emitting an excitation light beam of a second wavelength λ2, the second excitation light filter 105 for passing the excitation light beam of the second wavelength λ2 only, the second collimating lens 106 for converting the excitation light beam of the second wavelength λ2 into a parallel beam, and a second monitoring photodetector 126 for measuring an amount of the excitation light beam of the second wavelength λ2. In an embodiment, for example, the first excitation light filter 102 may be a band pass filter for passing a light beam of the first wavelength λ1 only. The second excitation light filter 105 may be a band pass filter for passing a light beam of the second wavelength λ2 only. However, in order to reduce a number of components and easily perform assembly, the first excitation light filter 102 and the second excitation light filter 105 may be the same band pass filter. In one embodiment, for example, the first and second excitation light filters 102 and 105 may each be a dual band pass filter that passes both the light beam of the first wavelength λ1 and the light beam of the second wavelength λ2.

The first fluorescence detection unit 115, 116, and 117 may include the first fluorescence filter 115 for passing a fluorescence beam with a third wavelength only, the fluorescence photodetector 117 for detecting the fluorescence beam with the third wavelength transmitted through the first fluorescence filter 115, and the first focusing lens 116 that is disposed between the first fluorescence filter 115 and the first fluorescence photodetector 117 and focuses the fluorescence beam with the third wavelength in the first fluorescence photodetector 117. In addition, the second fluorescence detection unit 119, 120, and 121 may include the second fluorescence filter 119 for passing a fluorescence beam with a fourth wavelength only, the second fluorescence photodetector 121 for detecting the fluorescence beam with the fourth wavelength transmitted through the second fluorescence filter 119, and a second focusing lens 120 that is disposed between the second fluorescence filter 119 and the second fluorescence photodetector 121 and focuses the fluorescence beam with the fourth wavelength in the second fluorescence photodetector 121. In this case, the first fluorescence filter 115 may be a band pass filter for passing the fluorescence beam with the third wavelength only. The second fluorescence filter 119 may be a band pass filter for passing the fluorescence beam with the fourth wavelength only. However, in order to reduce a number of components and easily perform assembly, the first fluorescence filter 115 and the second fluorescence filter 119 may be the same filter. In one embodiment, for example, the first and second fluorescence filters 115 and 119 may each be a dual band pass filter that passes both the fluorescence beam with the third wavelength and the fluorescence beam with the fourth wavelength.

The first automatic focusing unit 112, 113, 114, and 140 may include the actuator 112 for adjusting a focusing position of the objective lens 111, a third focusing lens 113 for focusing an excitation light beam of a first wavelength $\lambda 1$ reflected off the microfluidic device 150, the first divided-type photodetector 114 for detecting the excitation light beam of the first wavelength $\lambda 1$ reflected off the microfluidic device 150, and the focusing control unit 140 for calculating a focusing error from an output of the first divided-type photodetector 114 and for controlling an operation of the actuator 112. In addition, the second automatic focusing unit 112, 127, 128, and 140 may include the actuator 112, a fourth focusing lens 127 for focusing an excitation light beam of a second wavelength $\lambda 2$ reflected off the microfluidic device 150, the second divided-type photodetector 128 for detecting the excitation light beam of the second wavelength $\lambda 2$ reflected off the microfluidic device 150, and the focusing control unit 140 for calculating a focusing error from an output of the second divided-type photodetector 128 and for controlling an operation of the actuator 112. Thus, the actuator 112 and the focusing control unit 140 may be shared by the first automatic focusing unit and the second automatic focusing unit. In this case, the focusing control unit 140 may calculate an optimal focusing position (for example, an average focusing position) of the objective lens 111 from a focusing error of the excitation light beam of the first wavelength $\lambda 1$ and a focusing error of the excitation light beam of the second wavelength $\lambda 2$. If the first light source 101 is powered on and the second light source 104 is powered off, the focusing control unit 140 may consider only the focusing error of the excitation light beam of the first wavelength $\lambda 1$. On the other hand, if the first light source 101 is powered off and the second light source 104 is powered on, the focusing control unit 140 may consider only the focusing error of the excitation light beam of the second wavelength $\lambda 2$.

The light transferring unit 122, 123, 124, 125, and 129 may include a first beam splitter 122 that reflects and provides a portion of an excitation light beam of a first wavelength $\lambda 1$ of the first light source from the first light source 101, the first excitation filter 102 and the first collimating lens 103 to the first monitoring photodetector 109 and passes the remaining portion of the excitation light beam of the first wavelength $\lambda 1$, a first dichroic filter 123 that reflects the excitation light beam of the first wavelength $\lambda 1$ and passes a fluorescence beam with a third wavelength so as to provide the excitation light beam of the first wavelength $\lambda 1$ and the fluorescence beam with the third wavelength to the first fluorescence photodetector 117, a second beam splitter 125 that reflects and provides a portion of an excitation light beam of a second wavelength $\lambda 2$ of the second light source from the second light source 104, the second excitation light filter 105 and the second collimating lens 106 to the second monitoring photodetector 126 and passes the remaining portion of the excitation light beam of the second wavelength $\lambda 2$, a second dichroic filter 129 that reflects the excitation light beam of the second wavelength $\lambda 2$ and passes a fluorescence beam with a fourth wavelength so as to provide the excitation light beam of the second wavelength $\lambda 2$ and the fluorescence beam with the fourth wavelength to the second fluorescence photodetector 121, and a third dichroic filter 124 that reflects and provides the excitation light beam of the first wavelength $\lambda 1$ reflected off the first dichroic filter 123 to the microfluidic device 150 and passes and provides the excitation light beam of the second wavelength $\lambda 2$ reflected off the second dichroic filter 129 to the microfluidic device 150. The third dichroic filter 124 may reflect the fluorescence beam with the third wavelength generated by the microfluidic device 150, and may pass the fluorescence beam with the fourth wavelength generated by the microfluidic device 150. Thus, the third dichroic filter 124 may be a dual band dichroic filter for reflecting the excitation light beam of the first wavelength $\lambda 1$ and the fluorescence beam with the third wavelength and for passing the excitation light beam of the second wavelength $\lambda 2$ and the fluorescence beam with the fourth wavelength.

According to this structure, a portion of an excitation light beam of a first wavelength $\lambda 1$ emitted from the first light source 101 is reflected off the first beam splitter 122, and then is incident on the first monitoring photodetector 109. The remaining portion of the excitation light beam of the first wavelength $\lambda 1$ transmitted through the first beam splitter 122 is reflected by the first dichroic filter 123 and the third dichroic filter 124, and then is incident on the microfluidic device 150. Then, a fluorescence material labeling a sample in the chamber 151 of the microfluidic device 150 is excited by the excitation light beam of the first wavelength $\lambda 1$ and thus a fluorescence beam with a third wavelength is generated. Then, the excitation light beam of the first wavelength $\lambda 1$ and the fluorescence beam with the third wavelength are reflected by the third dichroic filter 124, and then are incident on the first dichroic filter 123. The first dichroic filter 123 reflects the excitation light beam of the first wavelength $\lambda 1$ towards the first beam splitter 122 and passes and provides the fluorescence beam with the third wavelength to the first fluorescence photodetector 117. A portion of the excitation light beam of the first wavelength $\lambda 1$ is reflected by the first beam splitter 122, and then is incident on the first divided-type photodetector 114.

In addition, a portion of an excitation light beam of a second wavelength $\lambda 2$ emitted from the second light source 104 is reflected off the second beam splitter 125, and then is incident on the second monitoring photodetector 126. The remaining portion of the excitation light beam of the second wavelength $\lambda 2$ transmitted through the second beam splitter 125 is reflected by the second dichroic filter 129, is transmitted through the third dichroic filter 124, and then is incident on the microfluidic device 150. Then, a fluorescence material labeling a sample in the chamber 151 of the microfluidic device 150 is excited by the excitation light beam of the second wavelength $\lambda 2$ and thus a fluorescence beam with a fourth wavelength is generated. Then, the excitation light beam of the second wavelength $\lambda 2$ and the fluorescence beam with the fourth wavelength are transmitted through the third dichroic filter 124, and then are incident on the second dichroic filter 129. The second dichroic filter 129 reflects the excitation light beam of the second wavelength $\lambda 2$ towards the second beam splitter 125 and passes and provides the fluorescence beam with the fourth wavelength to the second fluorescence photodetector 121. Then, a portion of the excitation light beam of the second wavelength $\lambda 2$ may be reflected by the second beam splitter 125, and then may be incident on the second divided-type photodetector 128.

Figure 9:
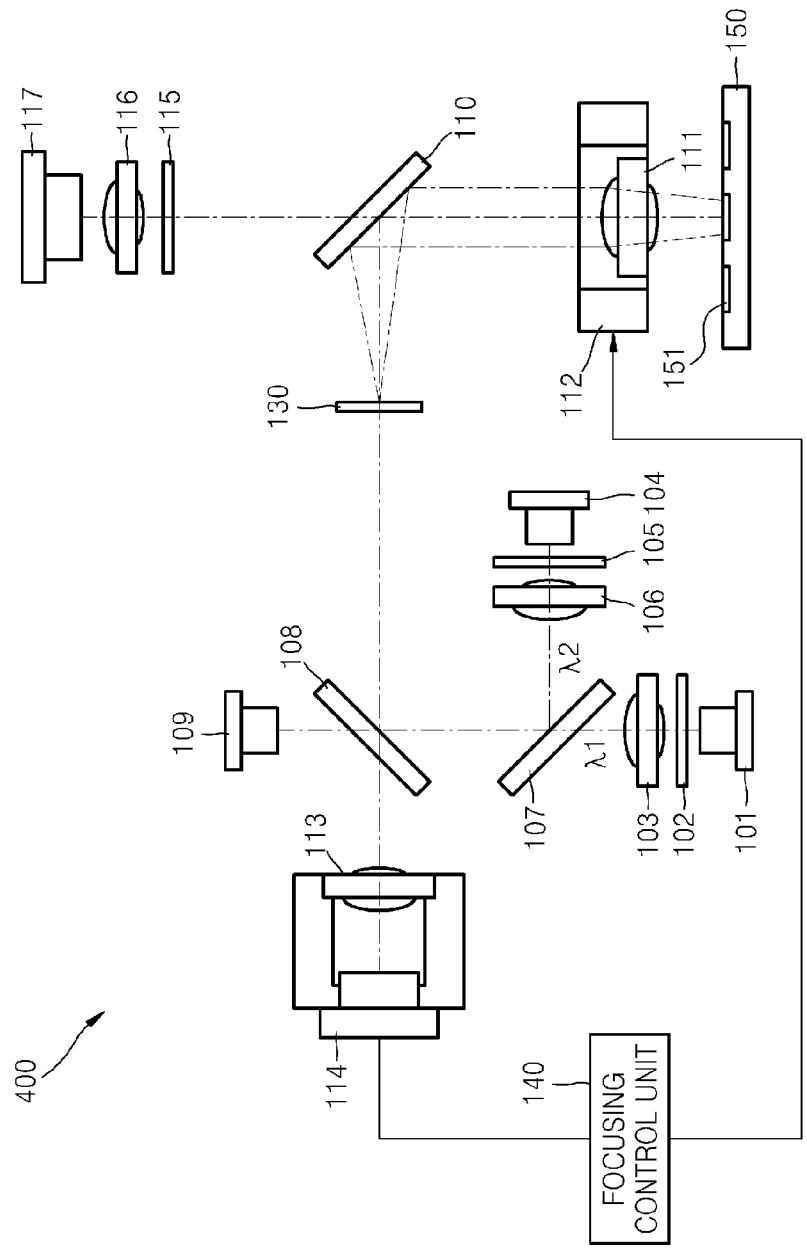
FIG. 9 is a schematic diagram of a fluorescence detection optical system, according to another embodiment of the present invention.

During detection of fluorescence, if there are impurities, bubbles, etc., on a position of the chamber 151 on which excitation light is focused, accuracy of detecting fluorescence and focusing accuracy may be reduced. In addition, if a sample is not uniformly distributed in the chamber 151, the accuracy of detecting fluorescence may also be reduced. FIG. 9 is a schematic diagram of a fluorescence detection optical system 400 for increasing accuracy of detecting fluorescence and focusing accuracy, according to another embodiment of the present invention. The fluorescence detection optical system 400 of FIG. 9 is different from the fluorescence detection optical system 100 of FIG. 1 in that the fluorescence detection optical system 400 further includes a diffraction grating 130 that is disposed between the beam splitter 108 and the second dichroic filter 110. In FIG. 9, the diffraction grating 130 is disposed between the beam splitter 108 and the second dichroic filter 110. Alternatively, the diffraction grating 130 may be disposed at any position on an optical path of excitation light between the beam splitter 108 and the objective lens 111.

Figure 10:
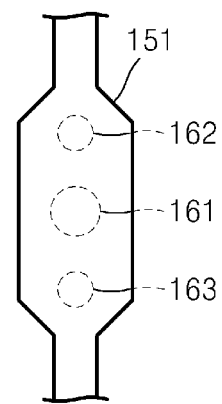
FIG. 10 is a schematic diagram showing a case where a plurality of optical spots are formed in a chamber by a diffraction grating of FIG. 9, according to an embodiment of the present invention.

The diffraction grating 130 diffracts excitation light so as to make a plurality of diffraction light beams. In an embodiment, for example, excitation light incident on the diffraction grating 130 may be divided into a $0^{th}$ order diffraction light beam and a $\pm 1^{st}$ order diffraction light beam. Then, as shown in FIG. 10, three focused optical spots 161 through 163 may be formed on the chamber 151. In one embodiment, for example, a first optical spot 161 of a central portion is formed by a $0^{th}$ order diffraction excitation light beam. Second and third optical spots 162 and 163 of two sides are formed by $\pm 1^{st}$ order diffraction excitation light beams, respectively. Since excitation light beams are focused on different positions on the chamber 151, even if there are impurities, bubbles, etc., on any one of the different positions, a reduction in accuracy of detecting fluorescence and focusing may be reduced or effectively prevented. In addition, even if a sample is not uniformly distributed in the chamber 151, fluorescence may be accurately detected. The diffraction grating 130 may also be used in the fluorescence detection optical systems 200 and 300 of FIGS. 7 and 8.

The above-described fluorescence detection optical systems 100, 200, 300, and 400 emit excitation light beams of different wavelengths, and detect two fluorescence beams with different wavelengths, but this is just an example, and the present invention is not limited to this. In an alternative embodiment, for example, a fluorescence detection optical system may be configured to emit a single excitation light beam only. In addition, a fluorescence detection optical system may be configured to emit three or more excitation light beams of different wavelengths.

The multi-channel fluorescence detection apparatus 500 of FIG. 6 includes two fluorescence detection optical systems 100 and 100' only, but the present invention is not limited to this. In one embodiment, for example, the multi-channel fluorescence detection apparatus 500 may include a single fluorescence detection optical system only, or alternatively, may include three or more fluorescence detection optical systems.

It should be understood that the embodiments described therein should be considered in a descriptive sense only and not for purposes of limitation. Descriptions of aspects within each embodiment should typically be considered as available for other similar features or aspects in other embodiments.

What is claimed is:

1. A fluorescence detection optical system comprising:
a light source unit which emits excitation light;
an objective lens which focuses the excitation light on a microfluidic device;
a fluorescence detector which detects fluorescence which is generated by the microfluidic device while a sample in the microfluidic device is excited by the excitation light;
an automatic focusing unit which detects the excitation light which is reflected off the microfluidic device, calculates a focusing error of the excitation light reflected off the microfluidic device, and adjusts a focusing position of the objective lens with respect to the microfluidic device; and
a light transferring unit which transfers the excitation light emitted from the light source unit to the microfluidic device, transfers the excitation light reflected off the microfluidic device to the automatic focusing unit, and transfers the fluorescence generated by the microfluidic device to the fluorescence detector,
wherein the automatic focusing unit comprises:
a divided-type photodetector which is divided into a plurality of photodetecting segments;
a focusing lens which focuses the excitation light reflected off the microfluidic device;
an actuator which adjusts the focusing position of the objective lens; and
a focusing control unit which calculates the focusing error from an output of the divided-type photodetector, and controls an operation of the actuator,
wherein the automatic focusing unit further comprises a knife edge which is between the focusing lens and the divided-type photodetector, and blocks out-of-focus light, and
wherein the divided-type photodetector is a dual-type photodetector comprising two photodetecting segments.

2. The fluorescence detection optical system of claim 1, wherein the focusing lens is an astigmatic lens, and
wherein the divided-type photodetector is a quad-type photodetector comprising four photodetecting segments.

3. The fluorescence detection optical system of claim 1, further comprising a diffraction grating which is between the light source unit and the objective lens, and divides the excitation light into a plurality of light beams which are incident on different positions of the microfluidic device.

4. A fluorescence detection apparatus comprising:
at least one fluorescence detection optical system of claim 1; and
a moving member which moves the at least one fluorescence detection optical system.

5. A fluorescence detection optical system comprising:
a light source unit which emits excitation light;
an objective lens which focuses the excitation light on a microfluidic device;
a fluorescence detector which detects fluorescence which is generated by the microfluidic device while a sample in the microfluidic device is excited by the excitation light;
an automatic focusing unit which detects the excitation light which is reflected off the microfluidic device, calculates a focusing error of the excitation light reflected off the microfluidic device, and adjusts a focusing position of the objective lens with respect to the microfluidic device; and
a light transferring unit which transfers the excitation light emitted from the light source unit to the microfluidic device, transfers the excitation light reflected off the microfluidic device to the automatic focusing unit, and transfers the fluorescence generated by the microfluidic device to the fluorescence detector,
wherein the light source unit comprises:
a first light source which emits an excitation light beam of a first wavelength;
a first excitation light filter which passes the excitation light beam of the first wavelength;
a second light source which emits an excitation light beam of a second wavelength which is different from the first wavelength; and
a second excitation light filter which passes the excitation light beam of the second wavelength,
wherein the light transferring unit comprises:
a first dichroic filter which faces the first light source and the second light source, passes the excitation light beam of the first wavelength emitted from the first light source, and reflects the excitation light beam of the second wavelength emitted from the second light source;

a second dichroic filter which is between the objective lens and the fluorescence detector, reflects the excitation light and passes the fluorescence generated by the microfluidic device; and a beam splitter which is between the first dichroic filter and the second dichroic filter, passes a portion of the excitation light incident on the beam splitter, and reflects a remaining portion of the excitation light incident on the beam splitter.

6. The fluorescence detection optical system of claim 5, wherein the first excitation light filter and the second excitation light filter are the same dual band pass filter, and wherein the band pass filter passes both a light beam of a first wavelength band and a light beam of a second wavelength band.

7. The fluorescence detection optical system of claim 5, wherein the second dichroic filter is a dual band pass dichroic filter which reflects the excitation light beams of the first and the second wavelengths, and passes fluorescence beams with third and fourth wavelengths generated by the microfluidic device.

8. The fluorescence detection optical system of claim 5, further comprising a monitoring photodetector which measures an amount of excitation light which passes from the first dichroic filter through the beam splitter.

9. The fluorescence detection optical system of claim 5, wherein the automatic focusing unit receives the excitation light which is reflected off the second dichroic filter and transmitted through the beam splitter.

10. The fluorescence detection optical system of claim 5, wherein the fluorescence detector detects the fluorescence generated by the microfluidic device and transmitted through the second dichroic filter, and wherein the fluorescence detector comprises:
a fluorescence filter which passes only fluorescence beams from among light passed through the second dichroic filter; and
a fluorescence photodetector which detects the fluorescence beams transmitted through the fluorescence filter.

11. The fluorescence detection optical system of claim 10, wherein the fluorescence filter is a dual band pass filter which passes only the fluorescence beams with third wavelength and the fluorescence beams with fourth wavelength generated by the microfluidic device.

12. The fluorescence detection optical system of claim 6, further comprising a plurality of fluorescence detectors, wherein
a first fluorescence detector detects fluorescence beams with a third wavelength from among light transmitted through the second dichroic filter;
a second fluorescence detector detects fluorescence beams with a fourth wavelength from among the light transmitted through the second dichroic filter; and
the light transferring unit further comprises a third dichroic filter which passes and transfers the fluorescence beams with the third wavelength from among the light transmitted through the second dichroic filter to the first fluorescence detector, and reflects and transfers the fluorescence beams with the fourth wavelength to the second fluorescence detector.

13. The fluorescence detection optical system of claim 12, wherein the first fluorescence detector comprises:

a first fluorescence filter which passes the fluorescence beams with the third wavelength from among the light passed through the third dichroic filter; and a first fluorescence photodetector which detects the fluorescence beams transmitted through the first fluorescence filter.

14. The fluorescence detection optical system of claim 13, wherein the second fluorescence detector comprises:
a second fluorescence filter which passes the fluorescence beams with the fourth wavelength from among the light reflected by the third dichroic filter; and
a second fluorescence photodetector which detects the fluorescence beams transmitted through the second fluorescence filter.

15. The fluorescence detection optical system of claim 14, wherein the first fluorescence filter and the second fluorescence filter are the same dual band pass filter, and
wherein the dual band pass filter passes both the fluorescence beams with the third wavelength and the fluorescence beams with the fourth wavelength.

16. A fluorescence detection optical system comprising:
a light source unit which emits excitation light;
an objective lens which focuses the excitation light on a microfluidic device;
a fluorescence detector which detects fluorescence which is generated by the microfluidic device while a sample in the microfluidic device is excited by the excitation light;
an automatic focusing unit which detects the excitation light which is reflected off the microfluidic device, calculates a focusing error of the excitation light reflected off the microfluidic device, and adjusts a focusing position of the objective lens with respect to the microfluidic device; and
a light transferring unit which transfers the excitation light emitted from the light source unit to the microfluidic device, transfers the excitation light reflected off the microfluidic device to the automatic focusing unit, and transfers the fluorescence generated by the microfluidic device to the fluorescence detector,
wherein the light source unit comprises:
a first light source which emits an excitation light beam of a first wavelength, and
a second light source which emits an excitation light beam of a second wavelength which is different from the first wavelength,
wherein the plurality of fluorescence detectors comprises:
a first fluorescence detector which detects a fluorescence beam with a third wavelength generated while the sample is excited by the excitation light beam of the first wavelength, and
a second fluorescence detector which detects a fluorescence beam with a fourth wavelength generated while the sample is excited by the excitation light beam of the second wavelength, and
wherein the plurality of automatic focusing units comprises:
a first automatic focusing unit which measures the excitation light beam of the first wavelength reflected off the microfluidic device, and performs an automatic focusing function, and
a second automatic focusing unit which measures the excitation light beam of the second wavelength reflected off the microfluidic device, and performs an automatic focusing function.

17. The fluorescence detection optical system of claim 16, wherein the light transferring unit transfers the excitation light beam of the first wavelength and the excitation light beam of the second wavelength to the microfluidic device, transfers the fluorescence beam with the third wavelength and the fluorescence beam with the fourth wavelength to the first fluorescence detector and the second fluorescence, respectively, and transfers the excitation light beam of the first wavelength and the excitation light beam of the second wavelength reflected off the microfluidic device, to the first automatic focusing unit and the second automatic focusing unit, respectively.

18. The fluorescence detection optical system of claim 17, wherein the light transferring unit comprises:

a first dichroic filter which faces the first light source and the first fluorescence detector, reflects the excitation light beam of the first wavelength, and passes and provides the fluorescence beam with the third wavelength to the first fluorescence detector;

a second dichroic filter which faces the second light source and the second fluorescence detector, reflects the excitation light beam of the second wavelength, and passes and provides the fluorescence beam with the fourth wavelength to the second fluorescence detector;

a first beam splitter which is between the first light source and the first dichroic filter, passes a portion of the excitation light beam of the first wavelength incident on the first beam splitter, and reflects a remaining portion of the excitation light beam of the first wavelength;

a second beam splitter which is between the second light source unit and the second dichroic filter, passes a portion of the excitation light beam of the second wavelength incident on the second beam splitter, and reflects a remaining portion of the excitation light beam of the second wavelength; and a third dichroic filter which faces the first dichroic filter and the second dichroic filter, reflects the excitation light beam of the first wavelength and the fluorescence beam with the third wavelength, and passes the excitation light beam of the second wavelength and the fluorescence beam with the fourth wavelength.

19. The fluorescence detection optical system of claim 18, further comprising:

a first monitoring photodetector which measures an amount of the excitation light beam of the first wavelength reflected by the first beam splitter from the first light source, and a second monitoring photodetector which measures an amount of the excitation light beam of the second wavelength reflected by the second beam splitter from the second light source.

20. The fluorescence detection optical system of claim 18, wherein the first automatic focusing unit receives the excitation light beam of the first wavelength reflected by the first dichroic filter and then reflected by the first beam splitter toward the first automatic focusing unit, and wherein the second automatic focusing unit receives the excitation light beam of the second wavelength reflected by the second dichroic filter and then reflected by the second beam splitter toward the second automatic focusing unit.

21. The fluorescence detection optical system of claim 20, wherein the first automatic focusing unit comprises:

a first divided-type photodetector which is divided into a plurality of photodetecting segments, and a first focusing lens which focuses the excitation light beam of the first wavelength reflected off the microfluidic device, and wherein the second automatic focusing unit comprises:

a second divided-type photodetector which is divided into a plurality of photodetecting segments, and a second focusing lens which focuses the excitation light beam of the second wavelength reflected off the microfluidic device.

22. The fluorescence detection optical system of claim 21, wherein the first automatic focusing unit and the second automatic focusing unit share:

an actuator which adjusts the focusing position of the objective lens; and a focusing control unit which calculates a focusing error of the excitation light beam of the first wavelength and a focusing error of the excitation light beam of the second wavelength, from outputs from the first divided-type photodetector and the second divided-type photodetector, and controls an operation of the actuator.

* * * * *